United States Patent [19]

Levinson

[11] Patent Number: 4,706,686
[45] Date of Patent: Nov. 17, 1987

[54] DIAGNOSTIC SCREENING PROCEDURE FOR IDENTIFYING DYSMETRIC DYSLEXIA

[76] Inventor: Harold N. Levinson, 600 Northern Blvd., Great Neck, N.Y. 11021

[21] Appl. No.: 923,598

[22] Filed: Oct. 27, 1986

[51] Int. Cl.⁴ ............................................. A61B 5/00
[52] U.S. Cl. ..................................... 128/745; 351/237
[58] Field of Search ................ 128/745; 351/211, 237; 352/240; 353/36, 46, 48, 71

[56] References Cited

U.S. PATENT DOCUMENTS

| | | | |
|---|---|---|---|
| 3,060,799 | 10/1962 | Myer | 353/48 |
| 3,317,151 | 5/1967 | Wright | 352/240 X |
| 3,416,857 | 12/1968 | Lookabaugh | 128/745 X |
| 3,842,822 | 10/1974 | Levinson et al. | 128/745 |
| 3,906,644 | 9/1975 | Levinson et al. | 351/237 X |
| 4,192,584 | 3/1980 | Dougherty | 353/48 X |

FOREIGN PATENT DOCUMENTS 0135686  5/1979  Fed. Rep. of Germany ...... 128/745

Primary Examiner—William E. Kamm
Assistant Examiner—Angela D. Sykes
Attorney, Agent, or Firm—Myron Amer

[57] ABSTRACT

Subjects possibly suffering from dysmetric dyslexia are screened by providing a visual display consisting of a plurality of discrete objects moving in a continuous line between a pair of spaced stationary objects. The subject reads the display from a distance at which normal subjects being screened are capable of seeing not only the moving objects but both stationary objects within their field of vision, and failing to see the entire display are identified as possibly being dyslexic.

6 Claims, 5 Drawing Figures

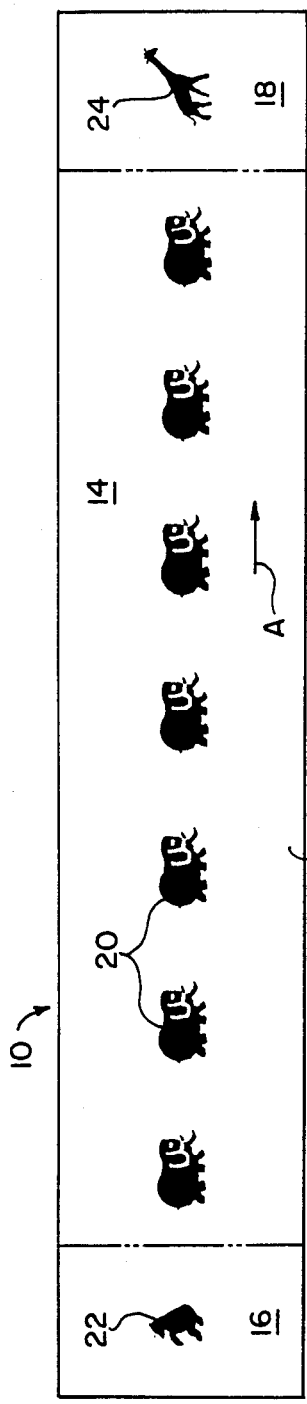
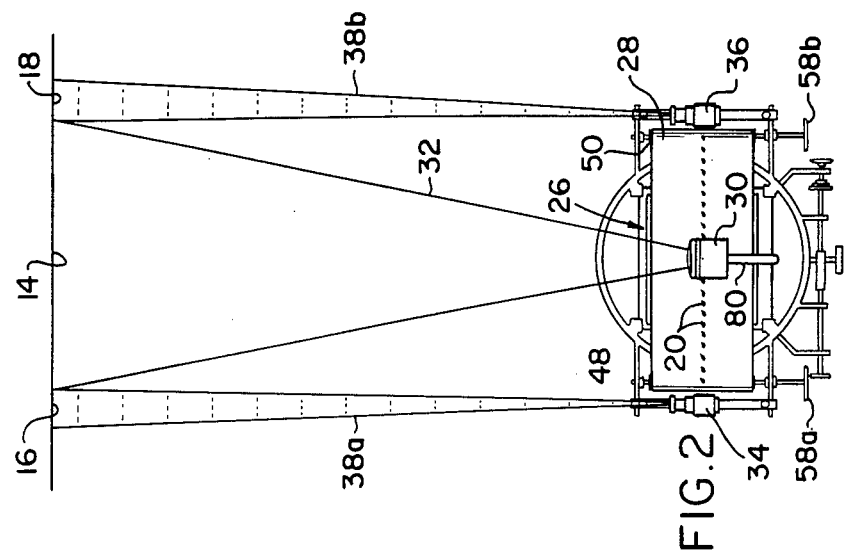
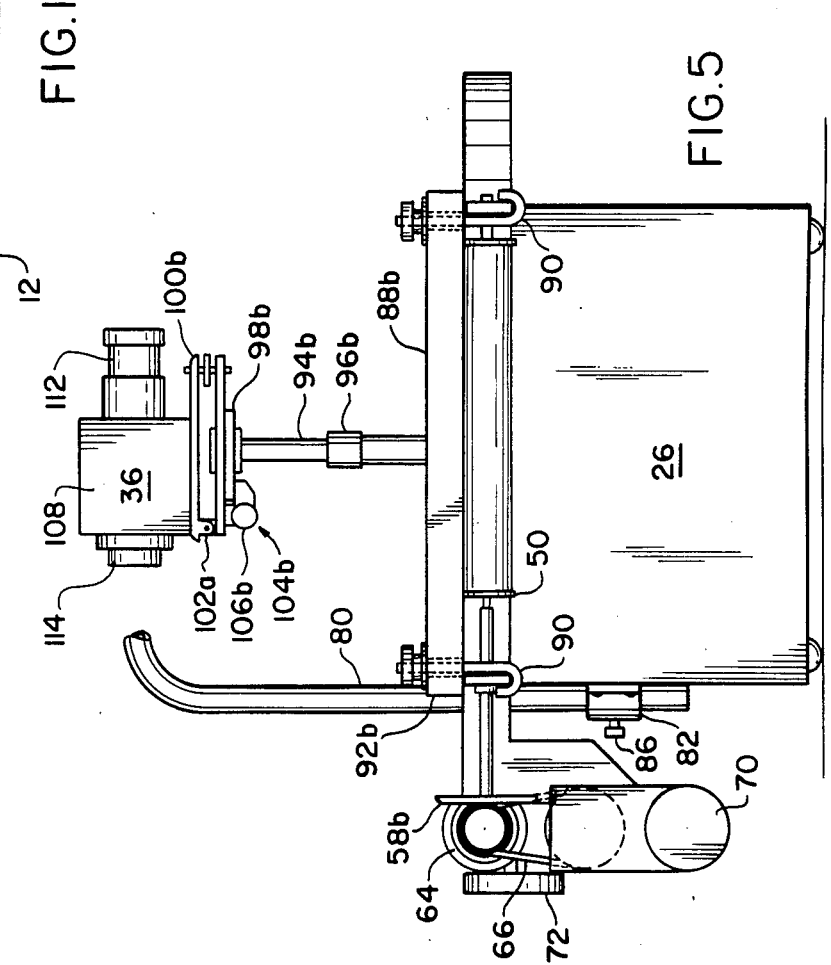

DIAGNOSTIC SCREENING PROCEDURE FOR IDENTIFYING DYSMETRIC DYSLEXIA

BACKGROUND OF THE INVENTION

The present invention relates to a screening procedure and apparatus for identifying children suffering from dysmetric dyslexia.

For well over a decade I have employed a technique disclosed in my U.S. Pat. No. 3,842,822 dated Oct. 22, 1974 by which dysmetric dyslexia was attributed to a cerebellar-vestibular dysfunction which I found can be detected by creating a subclinical nystagmus or eye vibration which resulted in the blurring of moving images when engaged in a reading type activity, i.e. visual fixation, tracking and sequential scanning, which induces the corresponding eye vibration or back and forth reading type eye movement. This movement or eye vibration occurs at a frequency or number of beats per second which can be controlled, being more specifically a function of the speed of movement of the material being visualized or read by the subject. Such induced eye vibration is maintained below the normal threshold level producing blurred vision in normal subjects, but which in additive relation to the subclinical eye vibration noted to exist in dysmetric dyslexic subjects, results in a total eye vibration at a frequency or number of beats per second above the threshold level. Accordingly, those subjects experiencing blurred vision during the reading process are automatically identified as possibly being dysmetric dyslexic.

After much experience I have discovered that contrary to the earlier thinking dysmetric dyslexic subjects have more than one blurring speed. While they have the same blurring speed as non-dyslexics do, i.e., a sequential blurring speed, in which a whole sequence of objects is seen as a panorama and the entire sequence blurs at once; they also have another blurring speed, which I call the single-targeting blurring speed. This latter phenomenon is a compensatory one, which takes over when the first, i.e., the reflexive, sequential tracking speed, is impaired. The single targeting blurring speed results from the observation that the subjects have an abnormally narrow lateral or peripheral span of vision. That is, they have practically no peripheral vision. This abnormality is observed when the subjects are forced to read a moving display and does not occur when reading a stationary display. For example, if the moving display is a continuous line of several discrete objects, the number of which in the field of vision always remaining the same, the subject would see less than the actual number displayed and when questioned as to the exact number seen, would provide an incorrect answer, since either the initial or the final members of the display (i.e. the peripheral members) would not be seen.

It is, therefore, the object of the present invention to provide a diagnostic procedure appropriate for individual or group examination for identifying dysmetric dyslexics employing the discovery mentioned above, namely, the inability of the subjects to maintain normal peripheral vision.

It is a further object of the present invention to provide a diagnostic procedure and apparatus for testing and identifying members of the subject groups having dysmetric dyslexia.

It is a further object of the present invention to provide a procedure and apparatus which is easily administered and which effectively screens individuals or members of large groups, particularly of children, for possible dysmetric dyslexia and to make a more rapid diagnosis of this affliction.

The foregoing objects and further objects as well as features and advantages of the present invention will be apparent from the following disclosure.

SUMMARY OF THE INVENTION

According to the present invention, the novel diagnostic screening procedure for identifying those subjects possibly suffering from dysmetric dyslexia comprises the steps of providing a visual display consisting of a plurality of discrete objects moving in a continuous line between a pair of spaced stationary objects. The entire display is first held stationary and the subject reads the display from a distance at which the subjects can normally see the entire display within their field of vision. Thereafter, the moving objects are set in motion, and those subjects which fail, thereafter, to see the entire display, i.e., those subjects whose field of vision does not include both terminal stationary objects as well as the lineally moving objects, are identified as possibly being dyslexic.

The foregoing procedure is, of course, based upon the discovery that dyslexic subjects have a significantly smaller lateral field of vision than persons not suffering from dysmetric dyslexia, and therefore, when concentrating on a moving display of discrete objects will fail to see one or both of the terminal stationary objects. The use of a visual display consisting of a plurality of discrete objects moving in a continuous line in a single plane insures that the subject will concentrate on the moving objects and be capable of determining the individual terminal stationary objects without being confused by any other blurring vision reaction. Accordingly, visual display although planar, is moved at a speed significantly less than the threshold level for blurring vision.

Preferably, the discrete objects in the moving display are identical to each other and are different from the terminal stationary objects, which terminal objects are preferably themselves different from each other. Preferably the objects are readily identifiable pictorial representations capable of being recognized even by the youngest of children.

It is preferred that the terminal stationary objects be intermittently visible as, for example, by stroboscopically flashing the objects into the screen, at a rate substantially equal to the linear movement of the series objects in the movable display. In the foregoing manner, any distraction from the purpose of determining the lateral or peripheral fields of vision are basically eliminated.

Full details of the present invention are set forth in the following description which includes the exemplary embodiment of the apparatus for practicing the same as disclosed in detail and illustrated in the accompanying drawings.

BRIEF DESCRIPTION OF THE DRAWINGS

FIG. 1 is a view of a visual display illustrating the procedure by which dysmetric dyslexia is determined;

FIG. 2 is an overall view showing in plan the apparatus for projecting the images and the lines of projection for forming the display shown in FIG. 1;

FIG. 5 is a side elevational view of the projection apparatus.

DESCRIPTION OF THE INVENTION

Figures 3, 4:
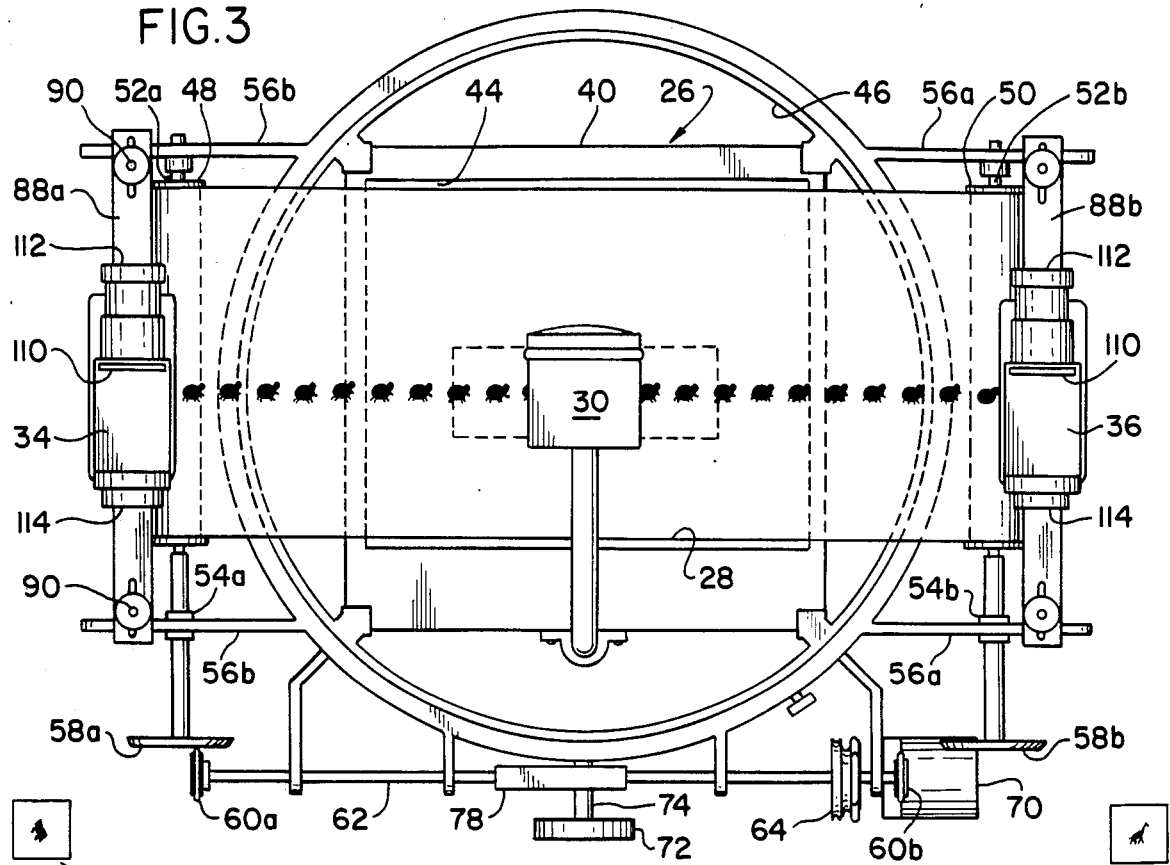
FIG. 3 is an enlarged plan view of the projection apparatus shown in FIG. 2.
FIG. 4 is an end elevational view of the projection apparatus.

Briefly, the procedure of the present invention can be illustrated and understood from reference to FIGS. 1 and 2, wherein a multipart display 10 is projected onto a screen 12. The display, as illustrated, comprises a central field 14 and flanking left and right terminal fields 16 and 18, respectively. Within the central field 14, a line of discrete uniformly spaced objects 20 are projected so as to move at a selected rate of speed, as illustrated in the example by the arrow A, from left to right. The objects 20, are shown in FIG. 1 as being animals, specifically, elephants for ease of identification. The form of the objects is not critical, except that they should be exactly the same size, shape, color and ornamentation so as to simplify their recognition and the total number in the field 14 without any difficulty, even by non dyslexic subjects. Further, the rate of speed at which the series of objects 20 are moved through the field 14, must be well below the threshold level of blurring, even for non dyslexic subjects.

Simultaneously, there is projected in each of the flanking fields 16 and 18 a different non-movable object, here illustrated again as an animal, namely, a bear 22 in the left field 16 and a giraffe 24 in the right field 18. The stationary objects 22 and 24 are different from the movable objects 20, so as to be easily distinguished and not confused with the movable objects even by non dyslexic subjects. The stationary objects 22 and 24 are flashed onto the flanking fields 16 and 18, for example, stroboscopically, at a rate substantially equivalent to that at which the individual movable objects 20 are moved across the central field 14.

Normal subjects, particularly children, at a given distance from the screen 12 will be able to see both flanking fields 16 and 18 as well as the central field 14 and will be able to determine the exact number of objects 20 within the central field 14 as well. On the other hand, it has been found that dyslexic children will be unable to see both flanking fields 14 and 16 simultaneously with a moving central field 14, and will be more than likely not to be able to count or determine the exact number of objects 20 within the central field, at the same time they view either one of the peripheral flanking members.

The diagnostic procedure, therefore, comprises placing the screen 12 and the subjects to be tested at a distance relative from each other, so that the subject is just barely able to see the entire display. The central field 14 is then caused to traverse across the screen, in the direction of arrow A, at a speed below the threshold level producing blurred vision, so that the subject will maintain clear imaging of the objects, and at the same time the flanking fields 16 and 18 are projected at the same rate or beat as the rate of travel of the central field 14. The subject is then required to optimally report (a) if he can see the entire screen, i.e., both flanking fields as well as the central field, (b) and if not, which of the flanking fields he sees and the number of objects in the central field. For younger children who are not sophisticated or adept, for example, at counting, the report can be simplified by determining which animals or, or how many different animals they, in fact, see. Any response less than the actual number present, enables the doctor to consider possible dysmetric dyslexia.

Manipulation of the speed of traverse of the central field 14, as well as the flashing of the flanking fields 16 and 18, can be made to determine the specific levels of dyslexia so that the level of dysfunction manifested by the subject can be determined and the subject further tested for the existence of this condition by any one or more of the other known and conventional tests for dysmetric dyslexia. Of course, it will be readily appreciated that the present diagnostic technique is extremely simple and easy to administer as compared with the other known confirming tests, most of which are time consuming, difficult, and relatively expensive. The use of the present procedure effectively and advantageously reduces the number of subjects which are thus required to receive the more difficult and confirming examinations.

An apparatus by which the display is produced on the screen 12 is shown schematically in FIG. 2. The apparatus generally comprises a lightbox 26 across the top of which a transparency film strip 28 is moved in the direction A beneath a fixed projector 30. The projector 30 projects a beam 32 casting the image of the film strip on central field 14 of the screen 12. Mounted to each side of the fixed projector 30 is a stroboscope projector 34 and 36 each capable of receiving a slide and projecting an image in a flashing beam 38a and 38b onto the screen 12 in the flanking fields 16 and 18, respectively.

The apparatus for carrying out the present invention is illustrated in more detail in FIGS. 3–5. The light box 26 comprises a housing 40 in which an internal light source (not shown) is suitably disposed and on top of which a transparent supporting plate 44 is fixed. A slip ring 46 is mounted about the periphery of the housing 40 to reciprocally rotate (arrow B) in a plane parallel to the supporting plate 44. The transparency film strip 28 containing the objects 20 is arranged to be moved across the plate 44, being entrained at one end about a feed roller 48 and at its other end about a take-up roller 50. The rollers 48 and 50 are identical and are mounted on central shafts 52a and 52b, respectively, which are freely journalled in spaced bearings 54a and 54b fixed to the slip ring 46 by brackets 56a and 56b so that the rollers 48 and 50 are parallel to each other and perpendicular to a diametric axis of the slip ring 46 across which the line of animal objects 20 on the film strip 28 passes. In this manner, the line or angle of movement of the film strip 28 relative to the screen 12 can be regulated by rotation of the supporting slip ring 46.

The feed and take-up rollers 48 and 50 respectively are alternatively driven in the forward or rewind direction by mounting at the rear end of each of the shafts 52a and 52b, a friction disc 58a and 58b, respectively engageable with a perpendicularly oriented drive disk 60a and 60b fixed at the ends of a freely rotatable and axially movable drive shaft 62. The drive shaft 62 is selectively shifted right to left, thereby causing alternate engagement of the respective driving discs 60a and 60b with the friction disks 58a and 58b of the feed roller 48, or the take-up roller 50. Fixedly mounted on the driving shaft 62 is a step pulley 64 having belt transmission 66 connected to the output shaft 68 of a unidirectional electric motor 70.

It will be readily appreciated that not only can the driving disks 60a and 60b selectively drive one or the other of the rollers 48 or 50, but by properly locating the selected driving disk 60a or 60b relative to the axis of rotation of the driven friction disk 58a or 58b control can be exercised over the speed at which the thus driven roller 48 or 50 rotates and thus the speed at which the transparency strip 28 is advanced over the supporting plate 44. Rewinding of the strip onto the feed roller 48 is easily accomplished by shifting the drive shaft 62 so that it engages the driven friction disk 58a associated with the feed roller 48. The drive shaft 62 is shiftable by manual operation of a knob 72, which is mounted on a stub shaft 74 on which is also fixed in pinion 76 (FIG. 4) meshing with a rack 78 integrally formed on the drive shaft 62.

It will be understood that the unidirectional drive motor 70 can be replaced with a reversible electric motor and the pulley and belt connection replaced with other transmission means. Similarly, a lever operated shifting mechanism can be substituted for the knob 72 and rack 76 and pinion 78.

The overhead projector 30 is arranged above the supporting plate 44 in proper projecting relationship to the transparency strip 28, being mounted on the end of an L-shaped cylindrical rod 80, secured in a bracket 82 mounted on the rear surface of the housing 40. Vertical positioning of the projector 30 can be achieved by providing the lower end of the cylindrical rod 80 with a series of annular grooves 84 into which a thumb screw 86 passing through the bracket 82 can be located. This also enables the pivoting of the projector 30 so that the proper angle between the transparency strip 28 and the display screen 12 as well as proper focusing of the projector 30 can be obtained and thereafter fixing the position securely.

The stroboscopic projectors 34 and 36, each designed to project the singular flanking images 16 and 18, respectively, onto the screen 12, are mounted on bridging members 88a and 88b fastened across each of the brackets 56a and 56b by jay hooks 90 (other fastening means may be used instead, if desired) so that each extends generally parallel to the rollers 48 and 50. Fixed to each of the bridging members 88a and 88b, approximately at their mid-point, is a base socket 92a and 92b into which a vertical telescoping shafts 94a and 94b are mounted. The telescoping shafts 94a and 94b are provided in two parts and have a central adjustment sleeve 96a and 96b enabling the height of each of the projectors 34 and 36 to be independently selected. Mounted on the upper end of the telescoping shafts 94a 94b is a platform support for the corresponding strobe projector comprising a lower plate 98a and 98b to which is pivotally hinged an upper plate 100a and 100b along their rear edges 102a and 102b. The lower plates 98a and 98b are secured to the upper end of the telescoping shaft 94a and 94b by an adjustable rotating mechanism 104a and 104b which maintains the plate 94a and 94b in a horizontal plane and permits its swinging adjustment relative to the axis of its associated shaft. The upper plates 100a and 100b are selectively positionable relative to its associated lower plate by an adjustable elevating screw mechanism 106a and 106b located at the forward edges of the plates. The stroboscopic projectors 34 and 36 are conventional units each comprising a central light box 108 having a slot (not shown) for the introduction of a slide, a focusing lens 112 and a stroboscopic or flashing control 114.

To insure that the central overhead projector 30 picks up and projects a predefined length of film strip 28, a mask (not shown) may be placed over the plate 44 (or the film strip 28, if so desired), thereby blocking out all but that part of the light passing through the transparent plate 44 which will insure projection of the predetermined number of objects 20 onto the screen 12.

In operation, the projection apparatus is arrayed with respect to the screen 12 so that the overhead projector 30 and the flanking stroboscopic projectors 34 and 36 can be focused properly so that each projects the beam 32 and 38a and 38b, as seen in FIG. 2 onto the fields 14, 16, and 18, respectively, of equal light intensity. The overhead projector 30 is arranged with or without the mask 116 so that the predetermined number of objects 20 are projected onto the screen, whereupon, the film strip 28 is caused to traverse across the table 44 at a speed selected so as to be well below the threshold level of blurring for the subject being tested. Simultaneously, the stroboscopic projectors 34 and 36 are turned on, and the intermittent pulsation of the beams 38a and 38b corresponding to the traversing of the objects 20 selected. The subjects are then requested to "read" either the number, type and form of the projected objects, the responses of which being recorded and thereafter analyzed by the doctor or tester.

Various changes, modifications, and substitutions have been suggested in the foregoing disclosure. Accordingly, it is intended that the disclosure be taken as illustrative only of the procedure and the apparatus of the present invention and is to be construed broadly in a manner consistent with the spirit and scope of the claims appended hereto.

What is claimed is:

1. A diagnostic screening procedure for identifying those subjects possibly suffering from dysmetric dyslexia comprising the steps of providing a visual display consisting of a plurality of discrete objects moving in a continuous line between a pair of spaced stationary objects, permitting the subject to read the display from a distance at which normal subjects being screened are capable of seeing both stationary objects within their field of vision, and identifying those subjects failing to see the entire display as possibly being dyslexic which is based upon the discovery that dyslexics have a significantly smaller peripheral field of vision than persons not suffering from dysmetric dyslexia.

2. The screening procedure according to claim 1, wherein said moving display comprises a series of discrete identical objects and each of said stationary objects are different from the objects in said series and from each other.

3. The screening procedure according to claim 1, wherein each of said objects are capable of ready identification by children.

4. The screening procedure according to claim 2, wherein said stationary objects are intermittently flashed on said display so as to be intermittently visible to the subject.

5. The screening procedure according to claim 4 wherein the intermittently visible stationary objects are flashed in said display at a selected rate equivalent to the linear movement of said series of discrete objects.

6. Apparatus for screening dysmetric dyslexia comprising a first film projector means for projecting a moving line of a plurality of discrete objects continuously across a screen and a pair of second film projectors means for stationarily projecting onto said screens flashing objects at each end of said moving line of objects, and means for regulating the speed of the flashing objects in correspondence with the continuously moving line of objects.

* * * * *